United States Patent [19]
Stropko

[11] Patent Number: 5,378,149
[45] Date of Patent: Jan. 3, 1995

[54] FLUID DISPENSING ASSEMBLY AND ADAPTER MEANS THEREFOR

[76] Inventor: John J. Stropko, 301 Parker Rd., Prescott, Ariz. 86303

[21] Appl. No.: 114,321
[22] Filed: Aug. 30, 1993
[51] Int. Cl.⁶ .......................................... A61G 17/02
[52] U.S. Cl. ...................................... 433/80; 433/81
[58] Field of Search .............................. 433/80, 81, 224

[56] References Cited

U.S. PATENT DOCUMENTS

| | | | |
|---|---|---|---|
| 1,417,379 | 5/1922 | Harvin | 433/91 |
| 1,958,332 | 5/1934 | Carpenter | 433/80 |
| 3,745,655 | 7/1973 | Malmin | 433/91 |
| 3,949,748 | 4/1976 | Malmin | 433/91 |
| 3,974,831 | 8/1976 | Malmin | 433/91 |
| 4,068,664 | 1/1978 | Sharp et al. | 433/91 |
| 4,248,589 | 2/1981 | Lewis | 433/80 |
| 4,353,693 | 10/1982 | Déry et al. | 433/27 |
| 4,384,852 | 5/1983 | Yamauchi et al. | 433/81 |
| 4,810,194 | 3/1989 | Snedden | 433/91 |
| 4,822,278 | 4/1989 | Oliva et al. | 433/91 |
| 4,878,900 | 11/1989 | Sundt | 604/119 |
| 5,013,300 | 5/1991 | Williams | 604/119 |
| 5,033,961 | 7/1991 | Kandler et al. | 433/80 |

OTHER PUBLICATIONS

*Thomas Scientific* 1988–89 Catalog; p. 1497; Swedesberg, N.J.
*Sigma-Aldrich Techware* 1993–94 Catalog; p. 294; St. Louis, Mo.
*Dental Products Report* (Advertisement); Jul., 1993; p. 25.

*Primary Examiner*—Cary E. O'Conner
*Attorney, Agent, or Firm*—Reising, Ethington, Barnard, Perry & Milton

[57] ABSTRACT

A fluid dispensing assembly 10 of the type for dispensing a precise stream of a fluid, such as a liquid and/or gas is disclosed. The fluid dispensing assembly 10 comprises of a fluid dispensing instrument or fluid source means 12, a needle apparatus 14, and is characterized by an adapter 16 for connecting the fluid dispensing instrument 12 to the needle apparatus 14 to establish fluid communication therebetween.

2 Claims, 3 Drawing Sheets

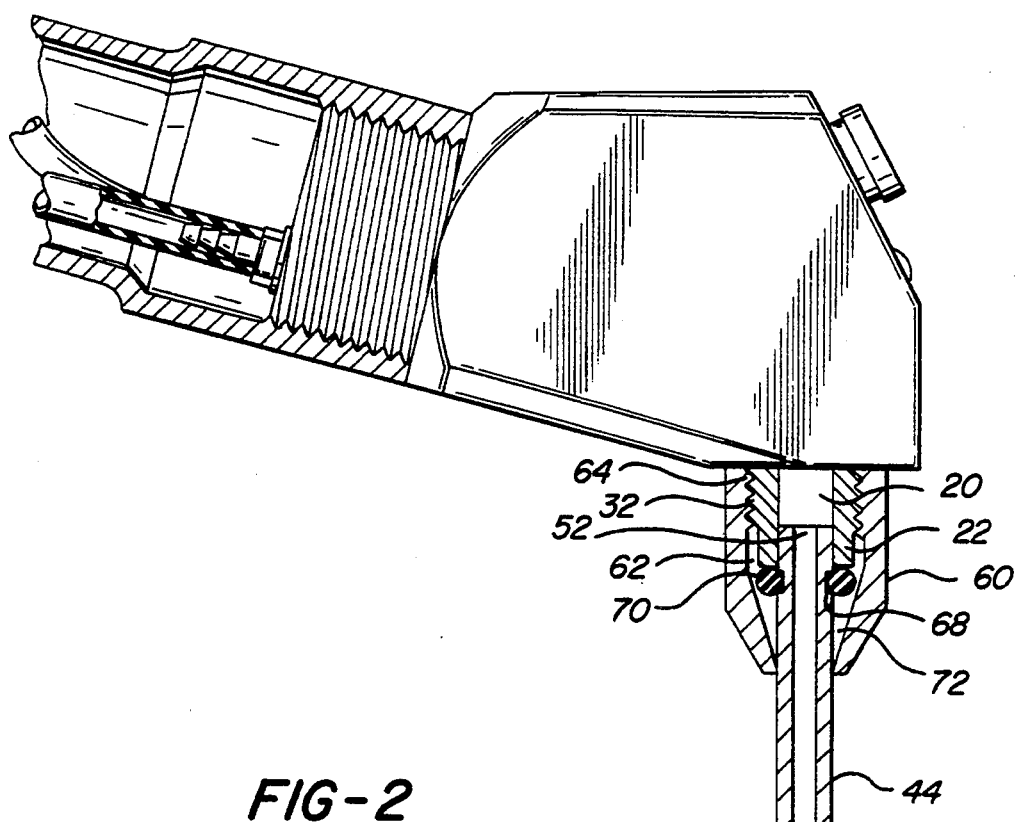
FIG-2
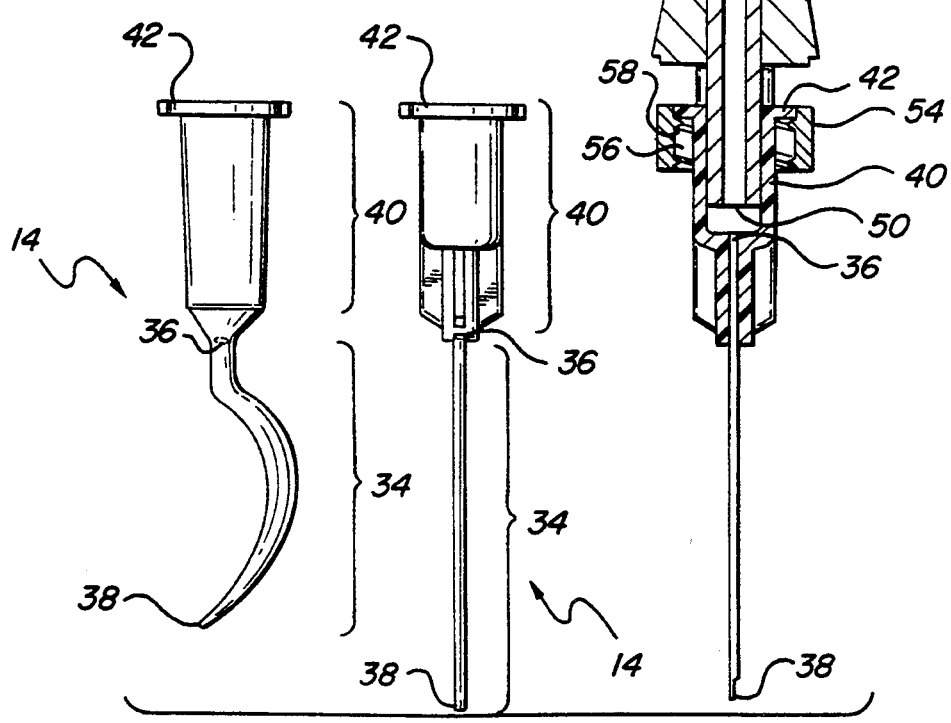

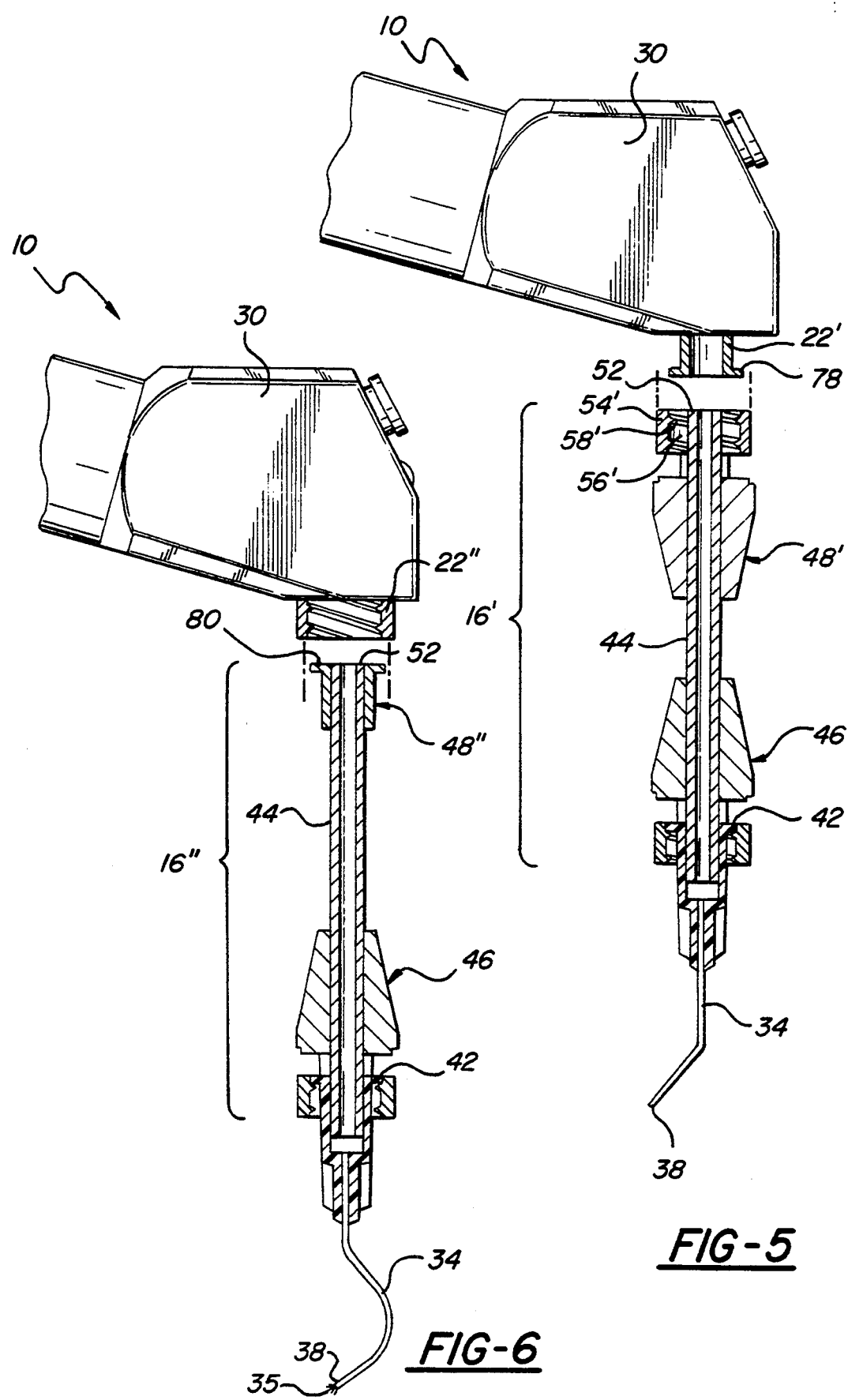

FLUID DISPENSING ASSEMBLY AND ADAPTER MEANS THEREFOR

TECHNICAL FIELD

This invention, in general, relates to assemblies for dispensing a precise stream of continuously pressurized fluid and adapters therefore.

BACKGROUND OF THE INVENTION

Many times it becomes necessary to dispense a precise stream of fluid to narrowly confined cavities. One example of this is in the application of water, medicine solutions, air, and the like to root canals and especially the apical foramen region of root canals. The prior art includes assemblies which directly connect, i.e. without the use of an adapter, a common needle apparatus of the type having a hollow needle and a hollow hub or needle-carrying member with a flange to a common hypodermic syringe of the type having a hollow barrel fitted with a plunger and a LUER-LOK ® (U.S. Reg. No. 306,120) nozzle. These assemblies can be used to provide a precise stream of fluid to a narrowly confined cavity but not without problems. Examples of this prior art can be found in U.S. Pat. Nos. 3,745,655 and 3,949,748. The hypodermic syringe used in these assemblies requires the user to manually move the plunger to dispense the fluid. In addition, the hypodermic syringe used in these assemblies provide a very limited source of fluid requiring frequent refilling of the syringe barrel. It thus becomes desirous to use a fluid dispensing system which utilizes a source of fluid under continuous pressure and a dispensing head of the type having an outlet and a valve to terminate the flow of the fluid through the outlet. However, the outlet of the dispensing head of these systems are not designed to directly connect to a LUER-LOK ® type needle. Instead, the outlet is usually designed to connect to a non-disposal and normally larger dispensing attachment not capable of accessing narrowly confined cavities, such as root canals.

The applicant is aware of adapters/connectors which connect LUER-LOK ® type needles to rubber or plastic tubing as illustrated on page 1497 of the THOMAS SCIENTIFIC ® 1988-89 catalog or on page 294 of Sigma-Aldrich Techware. However, these adapters/connectors cannot connect a LUER-LOK ® type needle to a fluid dispensing instrument capable of providing fluid under continuous pressure. Thus, the object of the present invention is to connect a LUER-LOK ® type needle to the outlet of a fluid dispensing instrument of the type capable of providing a fluid under continuous pressure to thereby enable a user to provide a precise stream of fluid to a narrowly confined cavity.

SUMMARY OF THE INVENTION AND ADVANTAGES

The fluid dispensing assembly of the present invention comprises of fluid source means or fluid dispensing instrument for supplying the fluid, a needle apparatus, and is characterized by an adapter for establishing fluid communication between the needle apparatus and fluid source means. The fluid dispensing instrument comprises fluid pressurizing means for maintaining the fluid under continuous pressure, a fluid supply line having an outlet for discharging the fluid from fluid pressurizing means, and a valve disposed the fluid supply line for terminating the flow of the fluid from the outlet.

The needle apparatus of the fluid dispensing assembly comprises a hollow needle for receiving the fluid at an inlet end thereof and discharging a precise stream of the fluid at a discharge end thereof and a hollow hub portion providing fluid communication to the inlet end of the hollow needle wherein the hollow hub includes a first flange.

The fluid dispensing assembly is characterized by an adapter for establishing fluid communication between the inlet end of the needle apparatus and outlet of fluid source means. The adapter comprises of a conduit extending between a first end and a second end for providing fluid communication between the ends thereof, a first connector positioned at the first end of the conduit for surrounding the first flange of the hollow hub to hold the first end of the conduit in the hollow hub to establish fluid communication between the first end of the conduit and the inlet end of the hollow needle, and a second connector positioned at the second end of the conduit for holding the second end in the outlet of the fluid source means to establish fluid communication therebetween.

The present invention also includes the adapter of the fluid dispensing assembly further characterized by the first connector having a cylindrical inner surface circumjacent and concentric to the conduit wherein the inner surface includes two identical spiral locking threads having starting ends spaced 180 degrees apart for surrounding and holding the first flange of the hollow hub. The adapter of the present invention is characterized by the second connector having a cylindrically shaped inner wall portion having at least one thread for surrounding the outlet of the fluid dispensing assembly and holding the second end of the conduit in the outlet.

The main advantage of the present invention over the prior art apparatuses is the provision of an adapter having the above noted characteristics which allows the connection of a fluid dispensing instrument of the type for dispensing a continuously pressurized fluid to a needle apparatus of the type having a hollow needle and a hollow hub with a flange thereby allowing the user of the instrument, needle apparatus, and adapter to dispense a precise stream of fluid to a narrowly confined cavity.

FIGURES IN THE DRAWINGS

Other advantages of the present invention will be readily appreciated as the same becomes better understood by reference to the following detailed description when considered in connection with the accompanying drawings wherein:

FIG. 2 is a sectional view of the preferred embodiment of the assembly and adapter of the present invention.

FIG. 5 is a exploded perspective view of a second embodiment of the assembly and adapter of the present invention.

FIG. 6 is a exploded perspective view of a third embodiment of the assembly and adapter of the present invention.

DESCRIPTION OF THE PREFERRED EMBODIMENT

Referring to FIGS. 1–4, a fluid dispensing assembly 10 of the type for dispensing a precise stream of a fluid, such as a liquid and/or gas is disclosed. The fluid dispensing assembly 10 comprises of a fluid dispensing instrument or fluid source means 12, a needle apparatus 14, and is characterized by an adapter 16.

Figure 1:
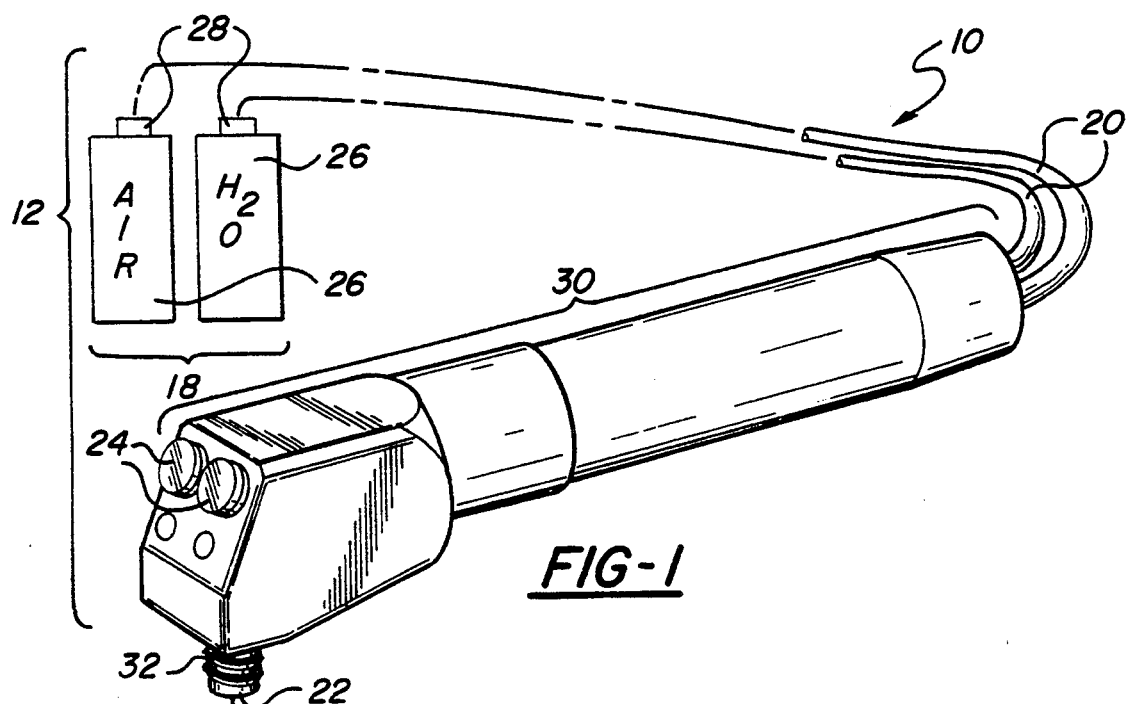
FIG. 1 is an exploded perspective view of the preferred embodiment of the assembly and adapter of the present invention.

Fluid source means 12 supplies the fluid and comprises of fluid pressurizing means 18 for maintaining the fluid under continuous pressure, a fluid supply line 20 having an outlet 22 for discharging the fluid from pressurizing means 18 and a valve 24 disposed in the fluid supply line 20 for terminating the flow of the fluid from the outlet 22. In the preferred embodiment as seen in FIGS. 1–4, fluid pressurizing means 18 comprises a tank 26 holding a fluid held under continuous pressure by a pump 28. As illustrated in FIG. 1, more than one tank 26 and pump 28 combination can be used wherein each combination holds and pressurizes a different fluid. In the preferred embodiment, one tank 26 and pump 28 combination holds and pressurizes water while the other combination holds and pressurizes air. For each tank 26 and pump 28 combination there is a corresponding supply line 20 leading to the outlet 22 and a corresponding valve 24 for terminating the flow of the corresponding fluid from the outlet 22. Thus, it is possible to have one or more different types of fluids exiting the outlet 22 at the same time. The outlet 22 and valves 24 are packaged in a metal housing or dispensing head 30. The dispensing head 30 is a readily available commercial unit. One such commercial unit, illustrated in the preferred embodiment of invention, is the Adec Three-way Syringe (Part #23-0084-00; Distributed by Adec, 2601 Crestview Drive, Newberg, Oreg. 97132). Another example of dispensing head 30 is the Spartan Syringe (Part #1107-086; Distributed by Forest Manufacturer, P.O. Box 989, Hillsboro, Oreg. 97123). The valves 24 in the preferred embodiment are spring-biased in a closed position. In the closed position, the fluid is prevented from exiting outlet 22. When an operator depresses and holds at least one valve 24 in the open position the pressurized fluid exits the outlet 22. The outlet 22 of the preferred embodiment, as illustrated in FIGS. 1–4, is cylindrically shaped and has a plurality of outlet threads 32 for connecting the outlet 22 to various attachment devices (not shown). It is important to point out that the outlet 22 can have at least two other embodiments as shown in FIGS. 5 and 6.

As shown in FIGS. 1–6, the assembly 10 also comprises a needle apparatus 14. The needle apparatus 14 comprises a hollow needle 34 for receiving the fluid at an inlet end 36 and discharging a precise stream of the fluid at a discharge end 38. The needle apparatus 14 also comprises a hollow tubular hub 40 providing fluid communication to the inlet end 36 of the hollow needle 34. The hollow hub 40 has a first flange 42 surrounding a hub opening 43. The hollow hub 40 is integrally molded to the hollow needle 34. Hollow hub 40 is commonly referred to as a LUER-LOK ® hub. The hollow hub 40 has an inside diameter 41. Although the gauge and length of the hollow needle 34 can vary, the inside diameter 41 of the hub 40 is always the same. Also, the first flange 42 always has the same shape. Typical gauges and lengths for the hollow needle 34 are from 14 to 30 and ½ inch to 6 inches, respectively. Hollow needle 34 can be made of plastic or metal. Likewise, the hollow hub 40 can be made of plastic or metal. The needle apparatus 14 can be either disposable or non-disposable. As seen in FIGS. 1–6, the hollow needle 34 can have varying shapes and, as shown in FIG. 6, can have blunting fibers 35 attached to the discharge end 38.

The hollow needle 34 is used by an operator to access a narrow cavity, such as a root canal. The operator can then use the discharge end 38 to deliver pressurized water, air, or a water/air mixture to the deepest portions of the narrow cavity, such as the apical foramen region of a root canal.

The assembly 10 is characterized by the adapter 16. The adapter 16 establishes fluid communication between the inlet end 36 of the needle apparatus 14 and the outlet 22 of the fluid source means 12. The adapter 16 comprises a conduit 44, a finest connector 46, and a second connector 48.

The conduit 44 extends between a first end 50 and a second end 52 to provide fluid communication between the ends 50, 52 thereof. The conduit 44 is tubular and is made from a rigid material, such as metal or plastic. The conduit has an outside diameter 45.

Figure 3:
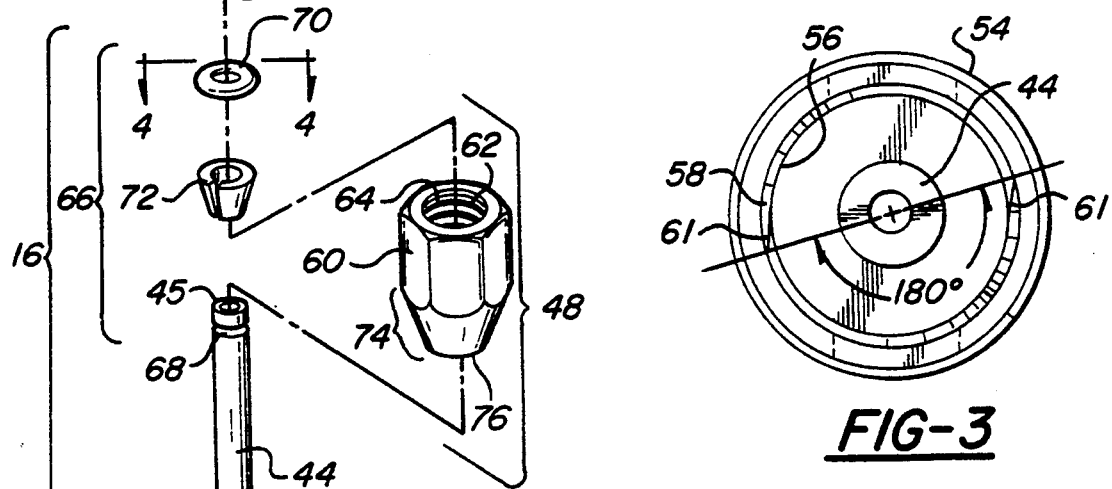
FIG. 3 is a sectional view taken along the lines 3—3 of FIG. 1.

The first connector 46 is positioned at the first end 50 of the conduit 44 and is designed to surround the first flange 42 of the hollow hub 40 to hold the first end 50 of the conduit 44 in the hollow hub 40 to establish fluid communication between the first end 50 of the conduit 44 and the inlet end 36 of the hollow needle 34. The first connector 46 comprises of an outer surface 54 and a inner surface 56. The inner surface 56 is cylindrical allowing the first connector 46 to receive and surround hollow hub 40. The inner surface 56 is circumjacent and concentric to the conduit 44 as shown in FIG. 3. A portion of the first end 50 of the conduit 44 protrudes beyond the confines of the inner surface 56. The inner surface 56 has two identical spiral locking threads 58 having starting ends 61 spaced 180 degrees apart for surrounding and holding the first flange 42 of the hollow hub 40. With this configuration, first connector 46 is commonly referred to as a LUER-LOK ® connector designed to engage with and lock LUER-LOK ® flanges such as first flange In practice, the first end 50 of the conduit 44 is inserted through hub opening 43 and into the hollow hub 40. The hollow hub 40 is then twisted in the clockwise direction about the conduit 44 until first flange 42 engages and is firmly locked between spiral locking threads 58. The inside diameter 41 of hub 40 is equal to the outside diameter 45 of the conduit 44. Thus, a fluid-tight seal is formed between the conduit 44 and the hub 40 preventing fluid from escaping through hub opening 43 and leaving the inlet end 36 of the hollow needle 34 as the only route of escape for fluid discharged from first end 50. The needle apparatus 14 can be removed from first connector 46 by twisting the hub 40 in the counter-clockwise direction until the first flange 42 is released from the grip of locking threads 58.

Figure 4:
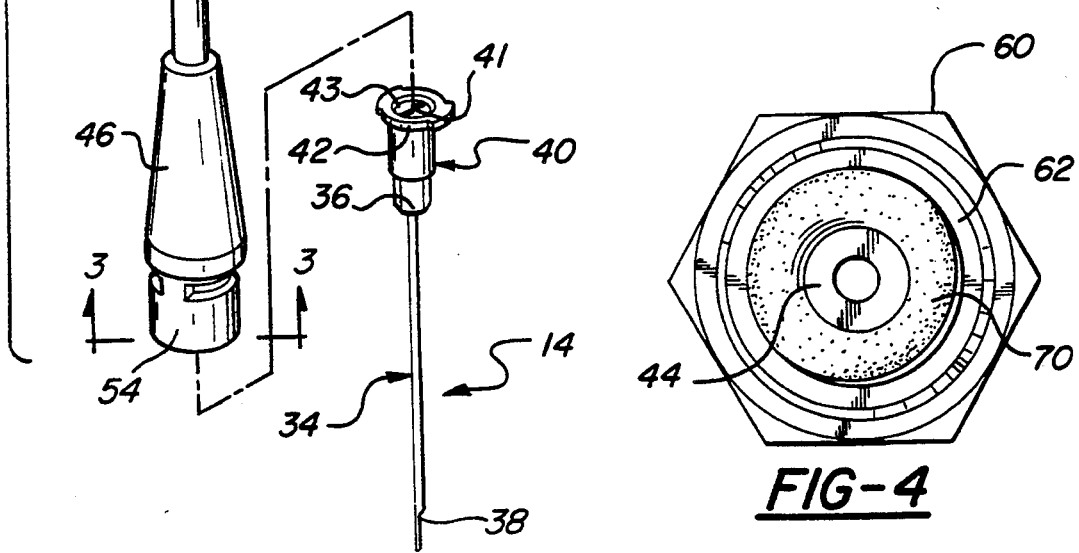
FIG. 4 is a sectional view taken along the lines 4—4 of FIG. 1.

The second connector 48 is positioned at the second end 52 of the conduit 44 to hold the second end 52 in the outlet 22 of the fluid source means 12 to establish fluid communication therebetween. The second connector 48 comprises an outer wall portion 60 and a cylindrically shaped inner wall portion 62 having at least one thread 64 for surrounding the outlet 22 of fluid dispensing instrument or source means 12 and holding the second end 52 of the conduit 44 in the outlet 22. As shown in FIG. 4, the inner wall portion 62 is circumjacent and concentric to the conduit 44.

The second connector 48 also includes a washer assembly 66 for holding the second connector 48 to the conduit 44. The washer assembly 66 includes a groove 68 about the conduit 44, a rubber ring 70 surrounding the conduit 44 and disposed in the groove 68, and a conical plastic spacer 72 surrounding the conduit 44 and adjacent the rubber ring 70.

The second connector 48 also comprises a conically shaped end section 74 extending from the inner wall portion 62 having an aperture 76 located at the apex for receiving the conduit 44. The spacer 72 of the washer assembly 66 is located within the conically shaped end section 74 for holding second connector 48 to the conduit 44. Unlike the first connector 46, the second connector 48 is rotatable and slidable about the conduit 44. This allows the operator to rotate the second connector 48 about the outlet 22 until the thread(s) 64 of the second connector 48 mesh and lock with the outlet threads 32. When the second connector 48 is tightened to the outlet 22, the second end 52 of the conduit 44 protrudes into the outlet 22. Also, the washer assembly 66 forms a fluid-tight seal between the outlet 22 and the second connector 48 such that the fluid exiting the outlet 22 enters only the second end 52.

FIGS. 5 and 6 illustrate two different embodiments of the adapter 16 having the identical features as described above and shown in FIGS. 1-4 except for the modifications described below. FIG. 5 shows the adapter 16' having the same first connector 46 but a different second connector 48 as described and shown in FIGS. 1-4. The second connector 48', shown in FIG. 5, has the same features and shape as first connector 46. The second connector 48' is designed to attach to an outlet 22' having a outlet flange 78 with a shape identical to first flange 42. The second connector 48' has a outer surface 54' and a inner surface 56'. The inner surface 56' is cylindrical allowing the second connector 48' to receive and hold the outlet 22'. The inner surface 56' is circumjacent and concentric to the conduit 44. A portion of the second end 52 of the conduit 44 protrudes beyond the confines of the inner surface 56'. The inner surface 56' has two identical spiral locking threads 58' having starting ends not shown but identical to starting ends 61 as shown in FIG. 3 and spaced 180 degrees apart for surrounding and holding the outlet flange 78 of the outlet 22'. With this configuration, the adapter 16' acts to extend the LUER-LOK ® type needle apparatus 14 away from the outlet 22' making it easier for an operator to access a narrow cavity.

FIG. 6 shows an adapter 16" having the same first connector 46 but a different second connector 48 as described and shown in FIGS. 1-4. The second connector 48" shown in FIG. 6, has a second flange 80 for holding the second connector 48" and the second end 52 of the conduit 44 in the outlet 22" of the fluid dispensing instrument or fluid source means 12. Second flange 80 has the same shape as first flange 42. The second flange 80 is designed to attach to an outlet 22" having a LUER-LOK ® connector identical to first connector 46.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

We claim:

1. A fluid dispensing assembly (10) of the type for dispensing a precise stream of fluid, said assembly (10) comprising:
   (a) fluid source means (12) for supplying the fluid, said fluid source means (12) comprising:
      (i) fluid pressurizing means (18) for maintaining the fluid under continuous pressure;
      (ii) a fluid supply line (20) having an outlet (22) for discharging the fluid from said pressurizing means (18), said outlet (22) having a plurality of exterior outlet threads (32); and
      (iii) a valve (24) disposed in said fluid supply line (20) for terminating the flow of the fluid from said outlet (22);
   (b) a needle apparatus (14) comprising:
      (i) a hollow needle (34) for receiving the fluid at an inlet end (36) thereof and discharging a precise stream of the fluid at a discharge end (38) thereof;
      (ii) a hollow hub (40) providing fluid communication to said inlet end (36) of said hollow needle (34), said hollow hub (40) having a first flange (42); and
   (c) an adapter (16) for establishing fluid communication between said inlet end (36) of said needle apparatus (14) and said outlet (22) of said fluid source means (12), said adapter (16) comprising:
      (i) a conduit (44) extending between a first end (50) and a second end (52) for providing fluid communication between said ends (50, 52) thereof;
      (ii) a first connector (46) positioned at said first end (50) of said conduit (44) and comprising a cylindrical inner surface (56) having two identical spiral locking threads (58) with starting ends (60) spaced 180 degrees apart for surrounding and holding said first flange (42) of said hollow hub (40) to hold said first end (50) of said conduit (44) in said hollow hub (40) to establish fluid communication between said first end (50) of said conduit (44) and said inlet end (36) of said hollow needle (34);
      (iii) a second connector (48) rotatably and slidably coupled about said second end (52) of said conduit (44) and comprising a cylindrically shaped inner wall portion (62) having at least one thread (64) for engaging said outlet threads (32) to connect said outlet (22) of said fluid source means (12) to said second connector (48) and to hold said second end (52) in said outlet (22) of said fluid source means (12) to establish fluid communication therebetween; and
      (iv) a washer assembly (66) for rotatably and slidably coupling said second connector (48) to said second end (52) of said conduit (44), said washer assembly (66) comprising a groove (68) about said conduit (44), a rubber ring (70) surrounding said conduit (44) and disposed in said groove (68), and a conical plastic spacer (72) surrounding said conduit (44) and adjacent said rubber ring (70).

2. An adapter (16) for connecting a fluid dispensing instrument (10) of the type having an outlet (22) for dispensing a fluid to a needle apparatus (14) of the type having a hollow needle (34) for receiving the fluid at an inlet end (36) thereof and discharging a precise stream of the fluid at a discharge end (38) thereof and a hollow hub (40) providing fluid communication to the inlet end (36) of the needle apparatus (14) wherein the hollow hub (40) includes a first flange (42); said adapter (16) comprising:

(i) a conduit (44) extending between a first end (50) and a second end (52) for providing fluid communication between said ends (50, 52) thereof;

(ii) a first connector (46) positioned at said first end (50) of said conduit (44) for surrounding the first flange (42) of the hollow hub (40) to hold said first end (50) of said conduit (44) in the hollow hub (40) to establish fluid communication between said first end (50) of said conduit (44) and the inlet end (36) of the hollow needle (34), said first connector (46) comprising a cylindrical inner surface (56) circumjacent and concentric to said conduit (44) wherein said inner surface (56) includes two identical spiral locking threads (58) having starting ends (61) spaced 180 degrees apart for surrounding and holding the first flange (42) of the hollow hub (40) thereby connecting the needle apparatus (14) to said first connector (46);

(iii) a second connector (48) rotatably and slidably coupled about said second end (52) of said conduit (44) for holding said second end (52) in the outlet (22) of the fluid dispensing instrument (10) to establish fluid communication therebetween, said second connector (48) comprising a cylindrically shaped inner wall portion (62) having at least one thread (64) for surrounding the outlet (22) of the fluid dispensing instrument (10) and holding said second end (52) of said conduit (44) in the outlet (22), a conically shaped end section (74) extending from said inner wall portion (62) and an aperture (76) located at the apex of said conically shaped end section (74) for receiving said conduit (44); and (iv) a washer assembly (66) for rotatably and slidably coupling said second connector (48) to said second end (52) of said conduit (44), said washer assembly (66) comprising a groove (68) about said conduit (44), a rubber ring (70) surrounding said conduit (44) and disposed in said groove (68), and a conical plastic spacer (72) disposed within said conically shaped end section (74) and surrounding said conduit (44) and adjacent said rubber ring (70).

* * * * *